US007747453B2

(12) United States Patent
Ulrich et al.

(10) Patent No.: US 7,747,453 B2
(45) Date of Patent: Jun. 29, 2010

(54) SYSTEM AND METHOD FOR MANAGING PATIENT ENCOUNTERS

(75) Inventors: Dennis A. Ulrich, London, KY (US); Burton E. Ulrich, Paducah, KY (US); Sandra I. Allen, Annville, KY (US)

(73) Assignee: Ulrich Medical Concepts, Inc., Paducah, KY (US)

( * ) Notice: Subject to any disclaimer, the term of this patent is extended or adjusted under 35 U.S.C. 154(b) by 2895 days.

(21) Appl. No.: 10/207,739

(22) Filed: Jul. 27, 2002

(65) Prior Publication Data

US 2003/0028402 A1 Feb. 6, 2003

Related U.S. Application Data

(60) Provisional application No. 60/310,412, filed on Aug. 6, 2001, provisional application No. 60/327,726, filed on Oct. 6, 2001.

(51) Int. Cl.
*G06Q 10/00* (2006.01)
*G06Q 50/00* (2006.01)
*A61B 5/00* (2006.01)
*G06F 19/00* (2006.01)

(52) U.S. Cl. .................................. 705/2; 705/3; 705/4
(58) Field of Classification Search ............... 705/1, 705/2, 3, 4
See application file for complete search history.

(56) References Cited

U.S. PATENT DOCUMENTS

| 5,471,382 | A | * | 11/1995 | Tallman et al. | 600/300 |
| 5,664,109 | A | * | 9/1997 | Johnson et al. | 705/2 |
| 5,715,449 | A | * | 2/1998 | Peters et al. | 707/102 |
| 5,724,580 | A | * | 3/1998 | Levin et al. | 707/104.1 |
| 5,764,923 | A | * | 6/1998 | Tallman et al. | 705/3 |
| 5,772,585 | A | | 6/1998 | Lavin et al. | |
| 5,886,693 | A | * | 3/1999 | Ho et al. | 715/700 |
| 5,946,659 | A | * | 8/1999 | Lancelot et al. | 705/3 |
| 5,989,187 | A | * | 11/1999 | Clawson | 600/300 |
| 6,022,315 | A | * | 2/2000 | Iliff | 600/300 |
| 6,334,192 | B1 | * | 12/2001 | Karpf | 714/1 |
| 6,482,156 | B2 | * | 11/2002 | Iliff | 600/300 |
| 6,607,481 | B1 | * | 8/2003 | Clawson | 600/300 |
| 2002/0169635 | A1 | * | 11/2002 | Shillingburg | 705/2 |

OTHER PUBLICATIONS

Dennis A. Ulrich, Forward by Dennis A. Ulrich, M.D., How to Use the Team Chart Concept, 2001, pp. vi-viii, Ulrich Medical Concepts, East Bernstadt, KY.

* cited by examiner

*Primary Examiner*—Gerald J. O'Connor
*Assistant Examiner*—Amber Altschul
(74) *Attorney, Agent, or Firm*—Stockwell & Smedley, PSC

(57) ABSTRACT

A method and system for electronically maintaining medical records and to facilitate availability and use of information relating to patients, as well as other information used in the operation of a medical facility. The system stores information such as patient charts, medical histories of patients, insurance information, including documentation requirements of insurance companies, timelines for calendaring events, and dictionaries of commonly or repetitively used information. The system permits inputting of information relating to a patient encounter or appointment with a patient and inputting information on business related contacts, including information on patients, pharmacies, physicians and insurance companies. The system further facilitates tracking of patients and their medical status, prescription writing, printing of reports, and preparation of insurance forms, including electronic claim forms.

13 Claims, 20 Drawing Sheets

20

Add New Contact                                      ✕

Last Name [Patient]   First Name [Paula]
Company [            ]
Please check the appropriate box if this contact is a...
☑ Patient
☐ Pharmacy
☐ Physician or Health Care Provider
    ☐ Include Physician Quick Access List
    Unique Physician ID Number (UPIN) [          ]
    Signature Line Text (HCFA 1500 Box 31) [          ]
☐ Insurance Company
    Electronic Billing Defaults (EMC NSF 301)
    AAO 17 0 Receiver ID [          ]
    AAO 18 0 Organization Type [        ▼]
    CAO 23 0 Claim Edition Indicator [        ▼]
    DAO 05 0 Source of Payment [        ▼]

You must enter a last name or a company name.   [OK] [Cancel]

SEARCH DIAGNOSIS DICTIONARY　　　　　　　　　　　　　　　X

Query Key　　　　　　　　　　　　　　Query On　[Code ▼]
[_____] [Query]　　　　　　　　　Sort By　[Description ▼]

[Select] [Exhaustive Research] [Display Commonly Used Codes] [Print All]
[Add] [Edit] [Delete] [Print Entry] [Print List] [List to File] [Records to File] [Cancel]

List　　☐ Show Deleted Items　　☐ Show Comments　　Entries [724]

| | |
|---|---|
| Abdominal aneurysm without mention of rupture | 441.4 |
| Abdominal pain A | 789.2 |
| Abdominal pain B | 341.4 |
| Abdominal pain C | 654.7 |
| Abdominal pain D | 556.3 |
| Abdominal pain E | 541.7 |
| Abdominal pain F | 782.6 |
| Abdominal pain G | 740.4 |
| Abdominal pain H | 679.2 |

SEARCH PROCEDURE DICTIONARY                                          X

Query Key                          Query On    [ Description      ▼ ]
[                    ]  [ Query ]  Sort By     [ Description      ▼ ]

| Select | Exhaustive Research | Display Commonly Used Codes | Print All |

| Add | Edit | Delete | Print Entry | Print List | List to File | Records to File | Cancel |

List     ☐ Show Deleted Items    ☐ Show Comments      Entries    724

| | |
|---|---:|
| Ace Wrap | 4414 |
| Ampicilin | 7892 |
| CXR | 3414 |
| Arthritis Panel | 6547 |
| B12 Injection | 5563 |
| Culture Chlamidia | 5417 |
| Depo Prevara | 7826 |
| CBC | 7404 |
| Procedure X | 6792 |

150

Edit Procedure

Tabs: Chiropractic | DME | Enteral | Parenteral | DMEPOS | Oxygen | Text
Procedure | More Info | Even More Info | Payor | TPO | Dental | Ambulance

| | Code | Description |
|---|---|---|
| Select Procedure | 99211 | Level 1 Office or Other Visit |

Optional Modifiers [ ]  Pick from List → Available Modifiers
(Double Click to Choose)

Dates of Service: 02-21-2001
TO 02-21-2001

QB Medicare Claims

Place of Service: 11
Type of Service: 1
Unit Charge $: 18.17

View

Days or Units: 1   Rcvd $   Due $
Total Charge $: 18.17  0.00  18.17
Co-Payment $: 0.00  $0.00/0.00%

Fee Schedule: Medicare Fee Schedule: $18.17

Diagnosis Codes
784.0 Headache Faci — 152

EPSDT  EMG  COB
HCA 1500, Box 24K, Reserved for Local Use: [ ] [ ] [ ]

(Change INS Billing Status) ☐ Do NOT Bill Insurance

Internal Comments:

OK | Cancel | Apply | Help

CARE PLAN REMINDER DEFINITION

Description: Make an Appointment for Mammogram

Timeline Category: Appointment

Lead Time: 1 YEARS ▼

Repeat Count: 4 (How Many Additional Reminders?)

Repeat Interval: 1 YEARS ▼

COMMENTS: A yearly reminder to have a mammogram.

[ OK ]  [ Cancel ]

CARE PLAN REMINDER DEFINITION

Description: Select a New Mammogram Program

Timeline Category: Care Plan

Lead Time: 5 YEARS ▶

Repeat Count: (How Many Additional Reminders?)

Repeat Interval: ▶

Comments: 5 Years have gone by since your original mammogram care plan was decided upon and implemented. You probably want to reevaluate the patient's condition and choose an appropriate care plan.

[OK] [Cancel]

SYSTEM AND METHOD FOR MANAGING PATIENT ENCOUNTERS

CROSS REFERENCE TO RELATED APPLICATIONS

This application claims the benefit of U.S. Provisional Application Ser. No. 60/310,410, filed Aug. 6, 2001 and U.S. Provisional Application Ser. No. 60/327,726, filed Oct. 6, 2001, the contents of which are incorporated herein by reference.

AUTHORIZATION UNDER 37 CFR SEC. 1.71

A portion of the disclosure of this patent document contains material which is subject to (copyright) protection. The (copyright) owner has no objection to the facsimile reproduction by anyone of the patent document or the patent disclosure, as it appears in the Patent and Trademark Office patent files or records, but otherwise reserves all (copyright) rights whatsoever.

BACKGROUND OF THE INVENTION

1. Field of the Invention

The present invention relates generally to a system and method for electronically maintaining medical records and, in particular, to a system and method for managing patient encounters using an electronic medical records system.

2. Related Prior Art

It is commonly known that health care providers, such as physicians, produce large volumes of information which must be managed in order to service patients, as well as to interact and communicate with outside sources, such as laboratories and insurance companies. Such information includes patient medical histories and demographics, records of encounters with the patients, specific requirements of insurance providers, such as Medicare, billing record information, and other necessary information for conducting the business of a medical facility. The records maintained by the health care provider are continually updated with not only current medical information on patients, but also with current billing, payment and scheduling information for the patients.

In order to efficiently maintain this information, electronic medical records systems have been developed in an attempt to insure accurate and complete input of information, and to facilitate information processing, retrieval and reporting. These electronic record systems are intended to ultimately replace patient records maintained in paper files, and generally attempt to reduce the work load of medical personnel in processing the information contained in these records.

Although various advantages have been provided by electronic medical records systems currently available, there is a continuing need for a relational data base model which provides rapid access to all aspects of information generated in the medical office. Further, there is a need for such a relational data base model which provides an electronic tool for organizing staff of a medical practice into a team of people working together through use of the information provided in the system. Further, there is a need for such a system which will allow modifications to the system without requiring major software upgrades, including modifications which permit implementation of new coding or billing and new patient care management plans.

SUMMARY OF THE INVENTION

The present invention provides a method and system for electronically maintaining medical records including a central computer and a plurality of separate workstation computers which are connected to the central computer. The central computer acts to store a data base of information relating to a medical practice, including patient records, stored information for implementation into patient records, such as patient care plans, billing, payment and scheduling records, as well as any other records required for operation of the medical facility. The system generally includes information previously contained in paper documents, including patient charts, business related contact information and information required to facilitate tracking of patients and their medical progress. In addition, the present system facilitates compliance with third party insurance provider requirements, such as Medicare, and in particular, facilitates selection of information for claim forms in order to insure an optimum financial return through selection of appropriate procedure codes for a patient encounter.

In one aspect of the invention, a method of managing a patient encounter using an electronic medical records system is provided, including collecting and storing individual patient medical information on a computer, assigning an office visit procedure code level to an encounter with a patient, entering documentation of the encounter with the patient, performing an audit of the documentation during the encounter with the patient, and providing an indication to a user of a requirement to provide additional documentation to support the assigned procedure code level.

In a further aspect of the invention, a method of managing a patient encounter using an electronic medical records system is provided, including providing a care plan dialog screen for creating a time base care plan, entering a care plan description at the care plan dialog screen, entering a care plan category at the care plan dialog screen, and entering at least one reminder event for inclusion in the care plan.

Other objects and advantages of the invention will be apparent from the following description, the accompanying drawings and the appended claims.

BRIEF DESCRIPTION OF THE DRAWINGS

FIG. 3 illustrates a new contact dialog box for the system;

FIG. 7 illustrates a patient registration dialog box for the system;

FIG. 14 illustrates a dialog box for accessing a dictionary containing diagnosis codes for inclusion in an encounter;

FIG. 15 illustrates a dialog box listing procedures for inclusion in an encounter;

FIG. 17 illustrates a dialog box for editing a procedure entry;

FIG. 19 illustrates a dialog box for entering details of a reminder for inclusion in the care plan of the dialog box illustrated in FIG. 18; and FIG. 20 illustrates the dialog box of FIG. 19 with a further reminder for inclusion in the care plan of the dialog box of FIG. 18.

DETAILED DESCRIPTION OF THE PREFERRED EMBODIMENT

The present invention provides a method and system for electronically maintaining medical records and is particularly designed to eliminate the need for paper records, such as paper medical charts, and to facilitate availability and use of information relating to patients, as well as other information used in the operation of a medical facility.

Figure 1:
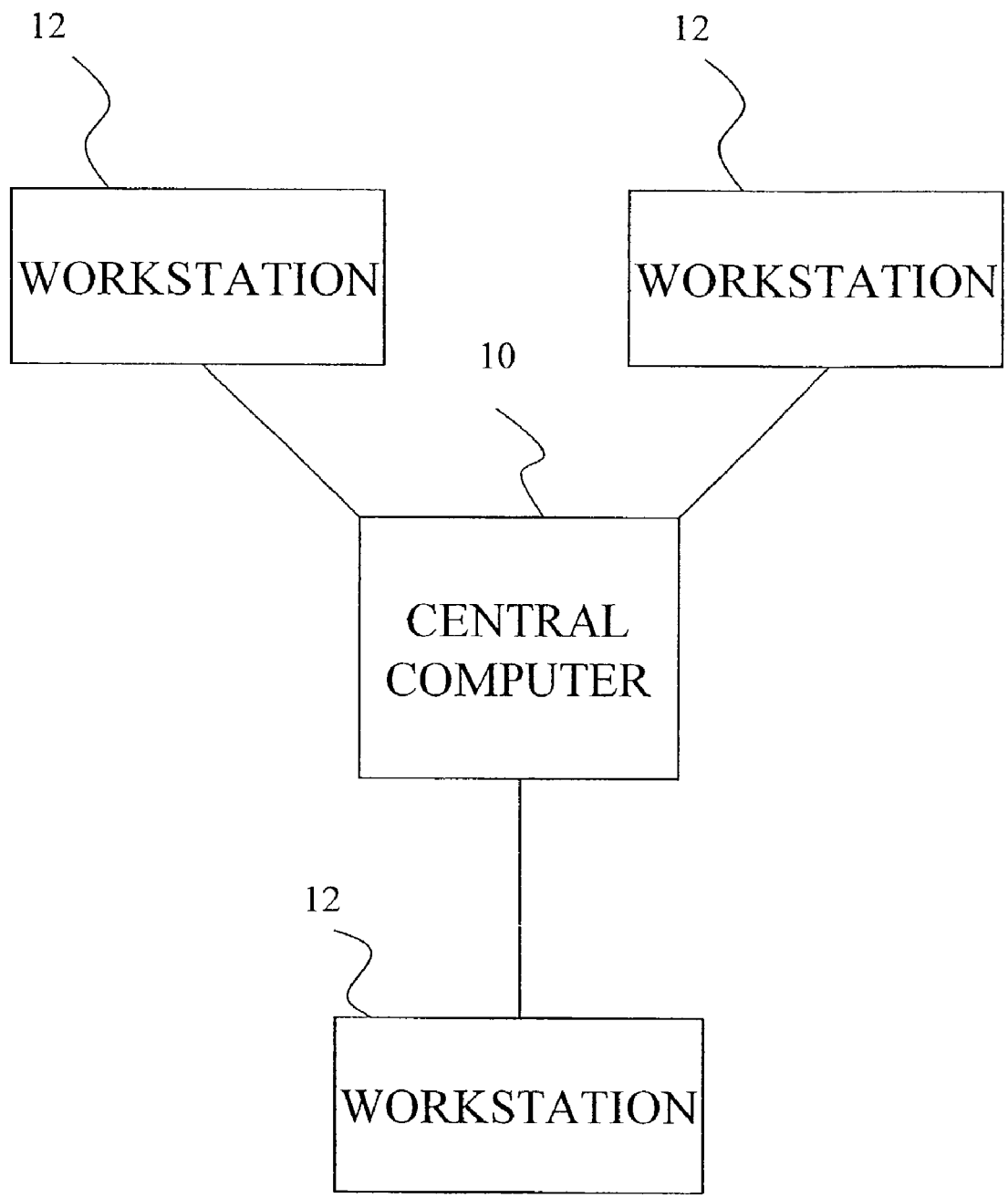
FIG. 1 is a diagramatic overview of the system of the present invention.

Referring to FIG. 1, the present invention preferably includes a central computer 10 and a plurality of separate workstation computers 12 connected to the central computer, such as through a conventional network system, and provides an efficient method of storing information and interfacing with a user for entering, accessing and outputting information to improve documentation and workflow. In particular, the system stores medical record information such as patient information, insurance information including documentation requirements of insurance companies, timelines for calendaring events, and dictionaries of commonly or repetitively used information. The dictionaries are groups of related entries (records). They may be viewed as reference material that does not change substantially over time and which may be selected for use during entry of data or for timeline entries. The dictionaries and their use will be described further below.

The present system is also designed to provide an interface for inputting data or information previously contained on paper documents, including inputting information relating to an encounter or appointment with a patient and inputting information on business related contacts including information on patients, pharmacies, physicians, and insurance companies. The system further provides outputs which facilitate tracking of patients and their medical status, prescription writing, printing of reports, and preparation of insurance forms including electronic claim forms and HCFA-1500 forms (Health Care Finance Administration forms) used to expedite Medicare, Medicaid and private insurance benefits.

Figure 2:
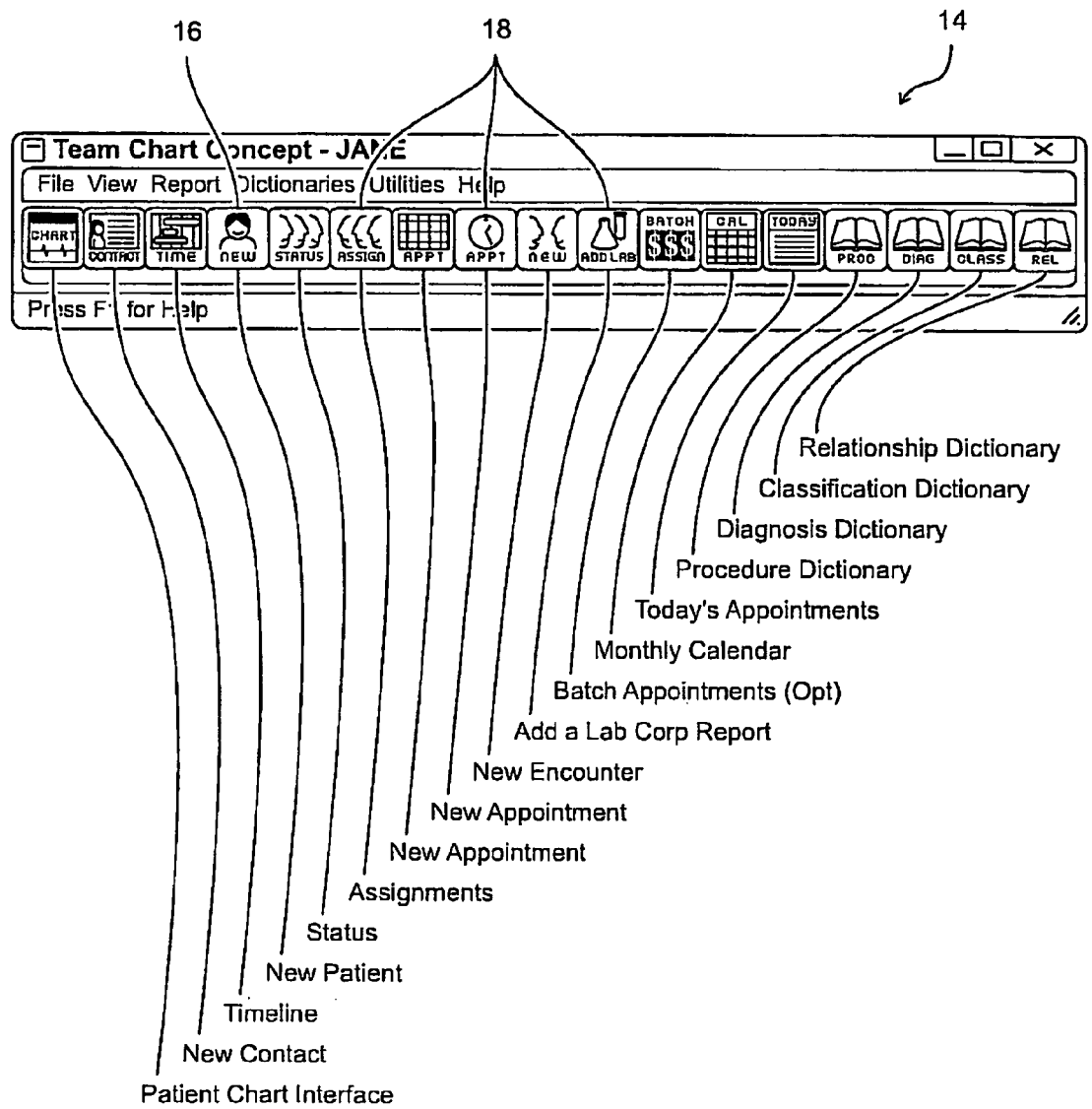
FIG. 2 illustrates a main screen for the system.

FIG. 2 illustrates a main screen 14 for the system and includes a toolbar 16 from which the most commonly used routines may be accessed. For example, buttons 18 on the tool bar 16 may be used to access appointment and calendar screens, access screens for preparing outputs such as reports, access screens for checking status of time dependent events, as well as other functions which are described below.

Figure 4:
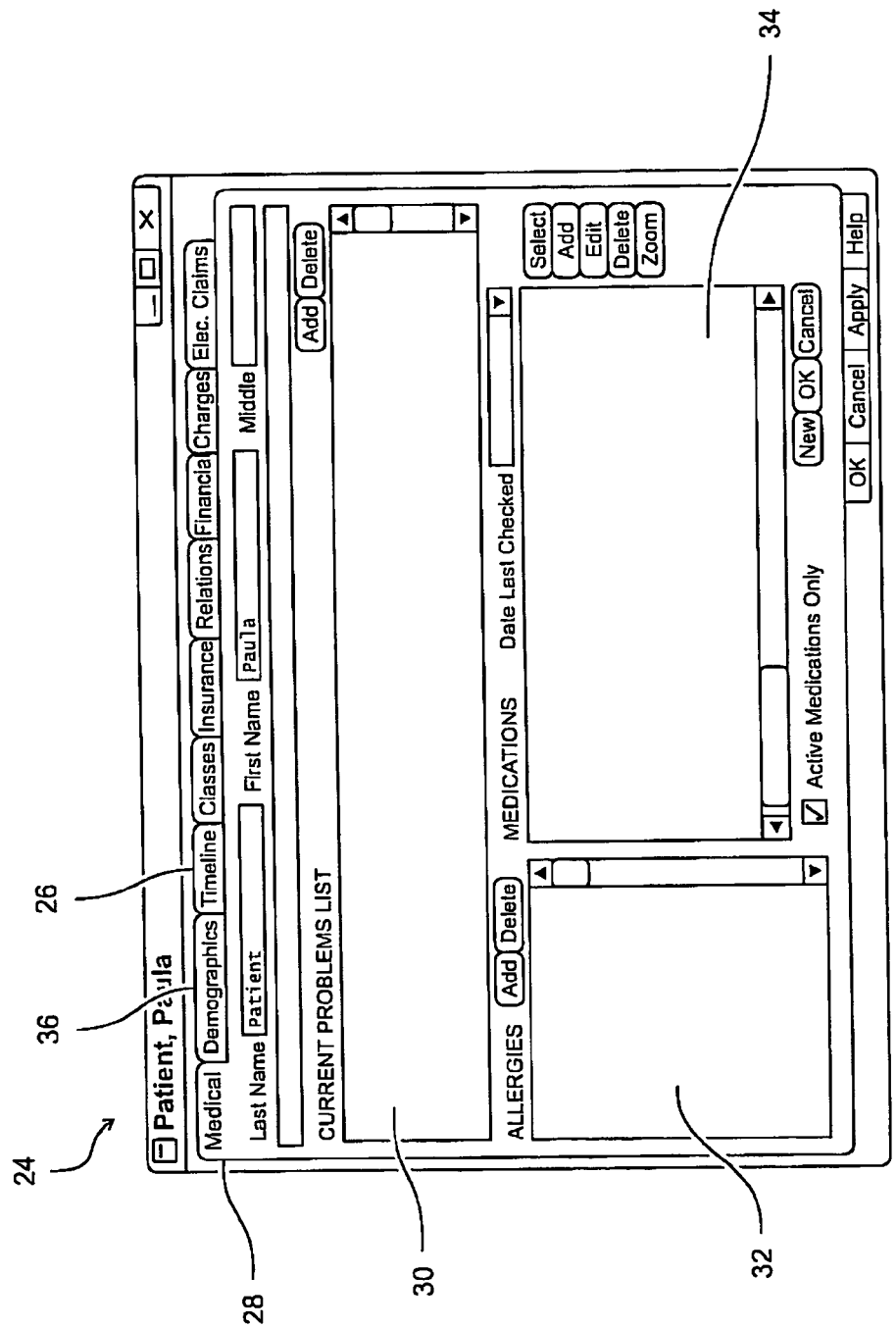
FIG. 4 illustrates a contact information dialog box for a particular patient, with a medical tab selected.
Figure 5:
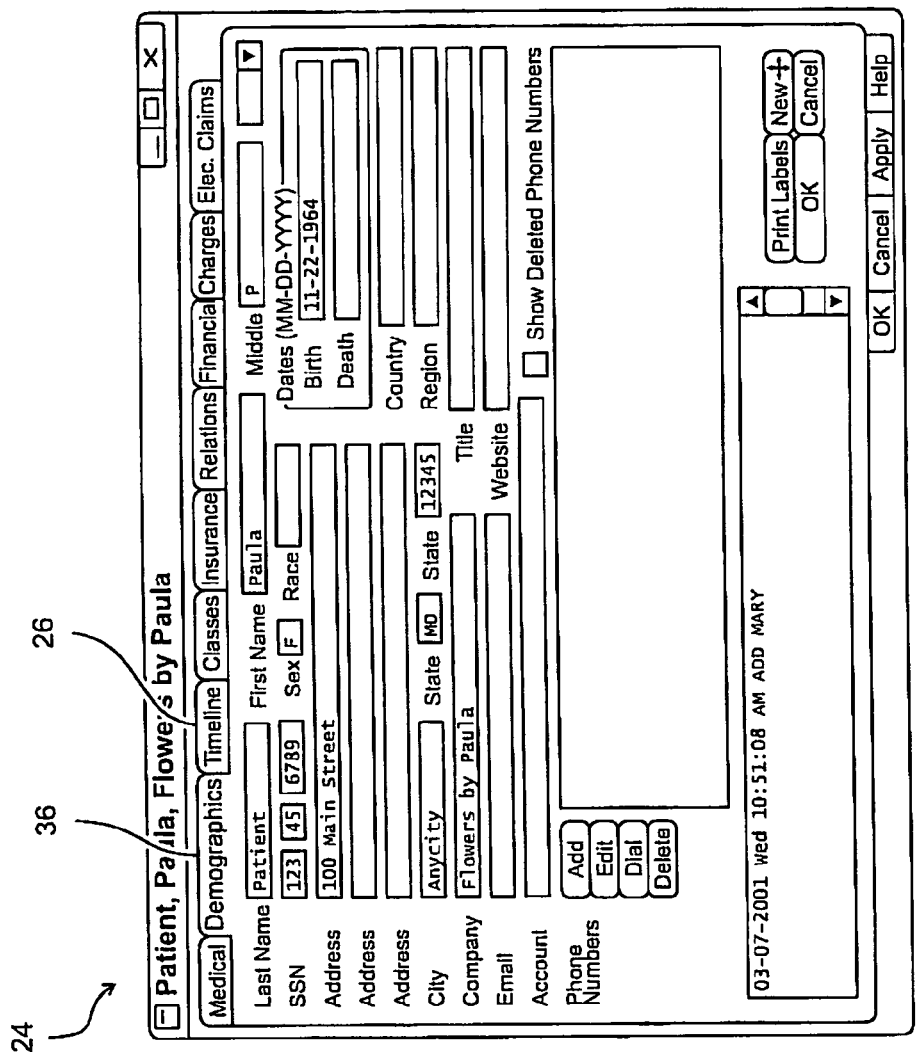
FIG. 5 illustrates the dialog box of FIG. 4 with a demographics tab selected.

Referring to FIG. 3, an Add New Contact dialog box 20 is illustrated which may be accessed from a screen called up by the Contacts button on the toolbar 16 of the main screen 14. The Add New Contact dialog box 20 is used to input contact information, such as for a patient, pharmacy, or health care provider, and in the illustrated example shows entry of a new patient. Upon entry of information in this dialog box 20, the user presses the OK button 22, which opens a Contact Information dialog box 24 (FIG. 4). It can be seen that the Contact Information fields for data entry. For example, in FIG. 4 the Medical tab 28 is selected for entering pertinent medical information into fields such as Current Problems 30, Allergies 32 and Medications 34. FIG. 5 shows the fields displayed upon selection of the Demographics tab 36 where pertinent contact information for the patient may be entered, such as address and phone numbers, as well as other demographic information such as birth date, social security number and employer.

Figure 6:
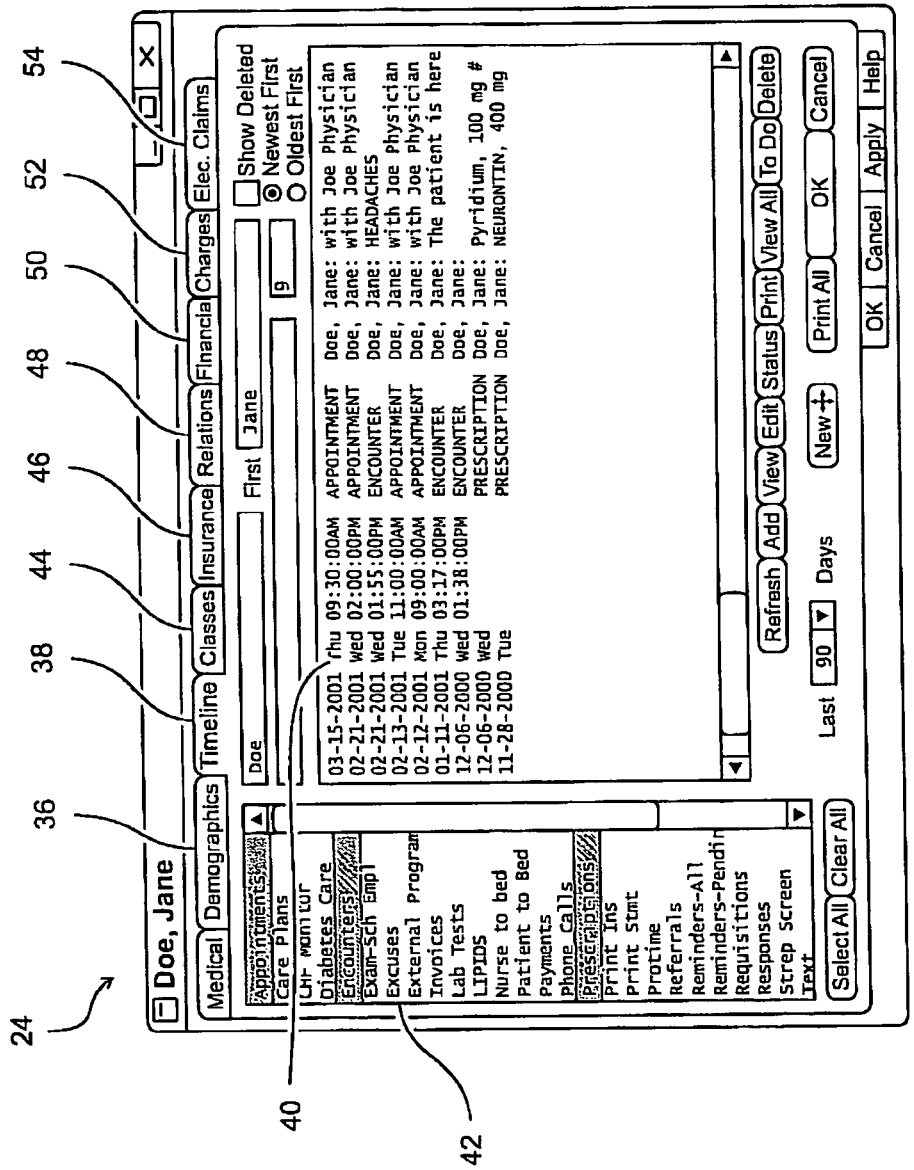
FIG. 6 illustrates the dialog box of FIG. 4 with a timeline tab selected.

FIG. 6 shows the fields displayed upon selection of the Timeline tab 38 which includes a main list box 40 listing a chronological history of evenly interaction with a contact, i.e., between a patient and the medical office. The list box 42 on the left side of the Contact Information dialog box 24 contains an alphabetical list of all available timeline entry types or categories. By selecting one or more of these timeline entry types, a list of timeline entries in the main list box 40 will be displayed for the selected contact. As used herein, "timeline" refers to the collection of date/time entries stored in chronological order in the system and including appointments, encounters (as defined below), prescriptions, excuses, referrals, lab results, payments, claims made to insurance companies, patient statements, user defined timeline records, and phone calls.

Additional information entered through selection of the remaining tabs 26 on the Contact Information dialog box 24 includes: Classes tab 44—includes fields for classification and categorization of contacts, i.e., patient, physician, nurse, insurance company, employee, pharmacy, etc., and collects status information (single, married, employed, etc.) required on the HCFA-1500 form; Insurance tab 46—lists all insurance companies associated with a particular patient; Relations tab 48 documents family relationships for the contact including contact type, i.e., son, and the name of the relation; Financial tab 50—used to review financial information on the patient, such as charges, money received and balance due, and provides for printing of statements and receipts; Charges tab 52—displays charges associated with a particular patient; Elec. claims tab 54—provides fields for entering patient defaults for use in filing electronic claims using the Electronic Media claims National Standard Format.

The information entered in the Contact Information dialog box 24 for a patient corresponds to information typically entered in paper chart systems upon registration of a new patient. It should be understood that pertinent contact information for physicians and pharmacies, as well as other contacts such as insurance companies, may be entered from the Contact Information dialog box in a similar manner to that described for patient information.

Figure 7:
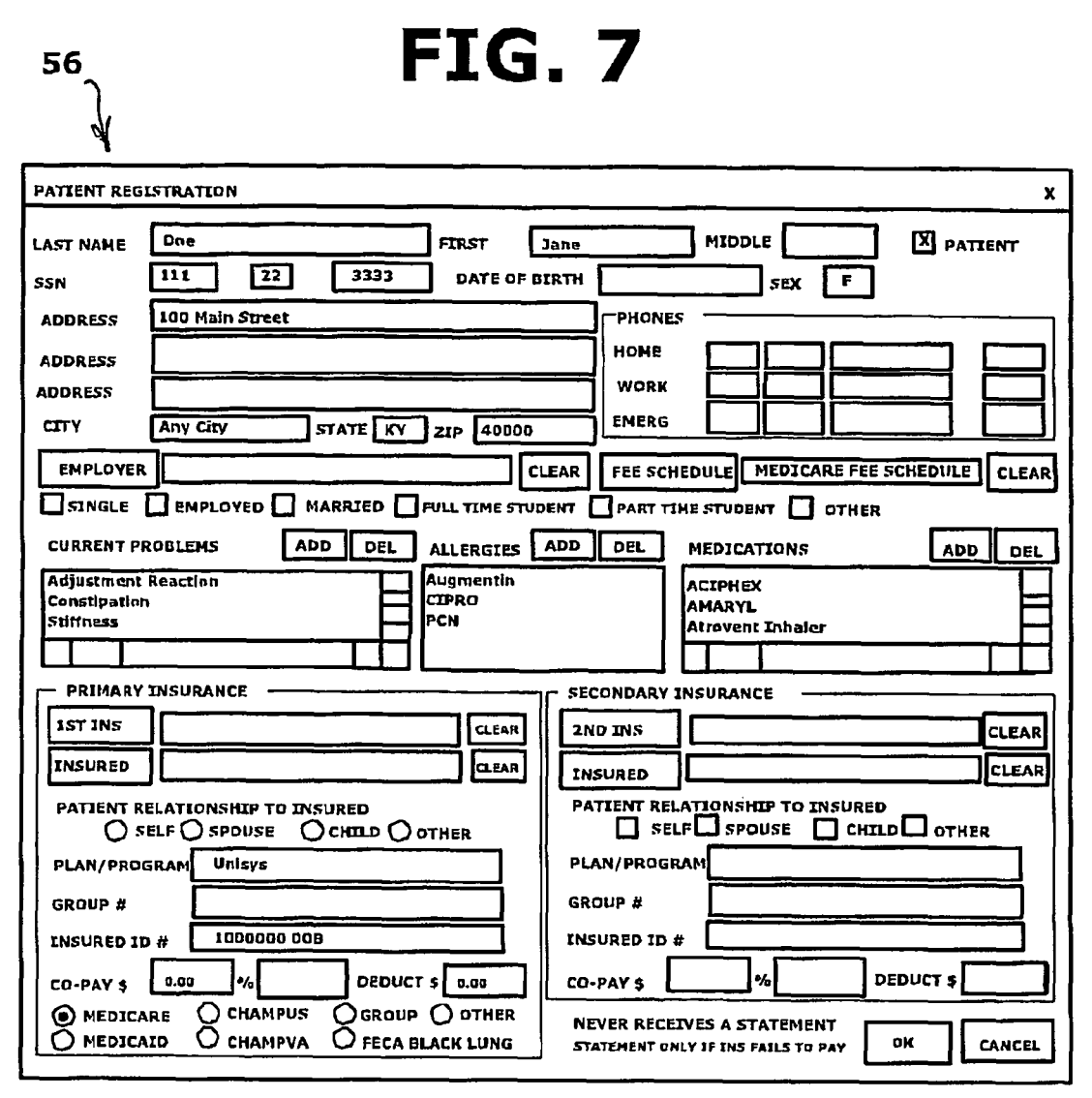

Referring to FIG. 7, a Patient Registration dialog box 56 is further provided for entry and display of information collected on any patient in the system, and this dialog box is accessed from the toolbar 16 (New Contact button) on the main screen 14. The information in this dialog box 56 is the same as is available in various places on the Contact Information dialog box 24 (FIG. 4), and the Patient Registration dialog box 56 conveniently provides the collected patient information at one reference location. It should be noted that it is possible to enter patient registration information through either the Patient Registration dialog box 56 or the Contact Information dialog box 24.

Figure 8:
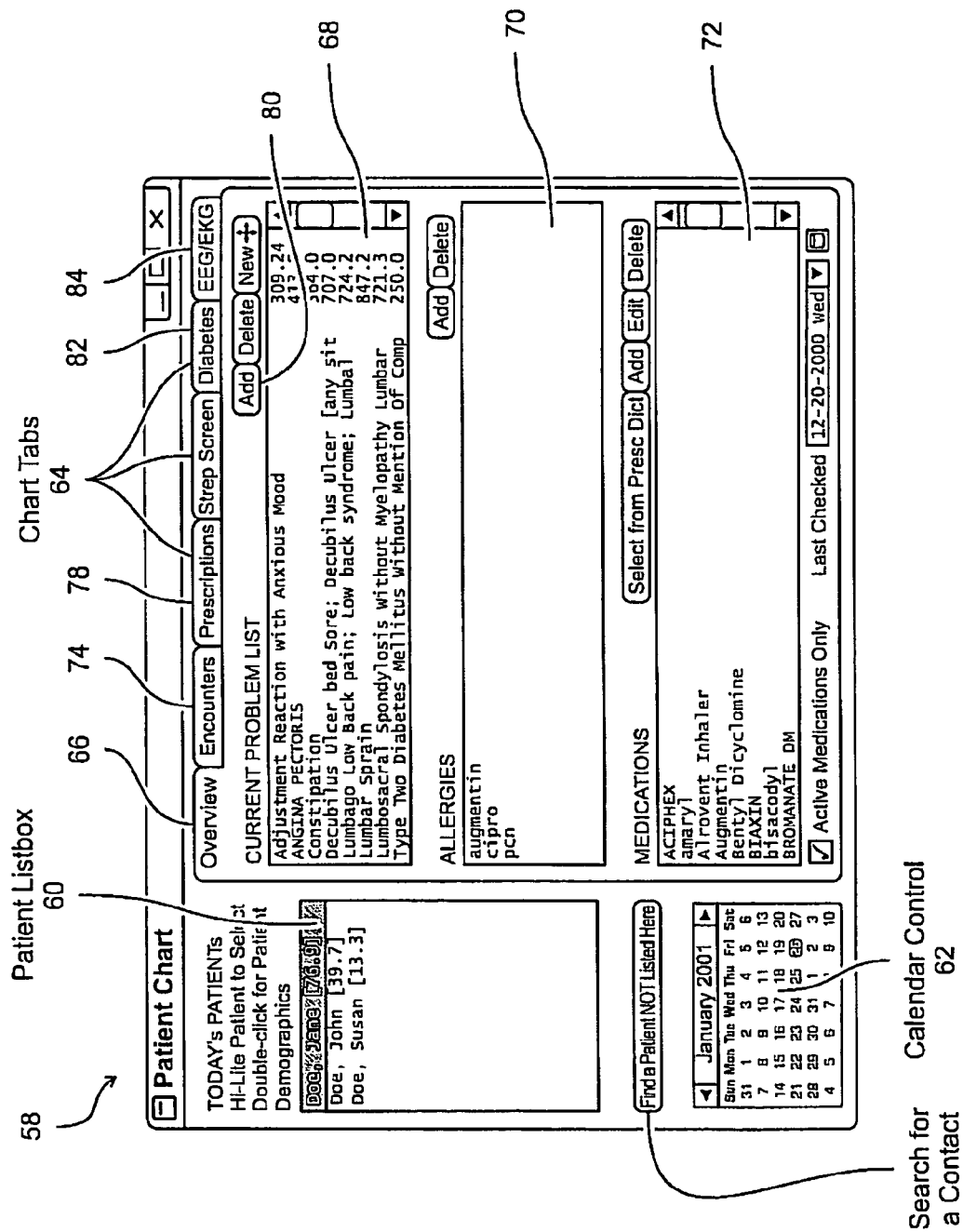
FIG. 8 illustrates a patient chart dialog box for the system, with an overview tab selected.

Referring to FIG. 8, a Patient Chart dialog box 58 is provided which is designed to generally correspond to the appearance of a paper chart, while providing enhancements available as a result of use of an electronic record system. The Patient Chart dialog box 58 generally includes a patient listbox 60, a calendar control 62, and a chart tabs area 64. The calendar control 62 specifies the date for listing patients in the patient listbox 60, and more specifically, lists patients who have an appointment or other date related activity ("timeline entry") for the selected date. The patient listbox 60 lists all patients having a timeline entry on the selected date, and a particular patient may be selected within this box to display the selected patient's chart. The chart tabs area 64 includes a plurality of tabs for displaying list boxes corresponding to different categories of medical information for the patient wherein all tabs except for the overview tab 66 are timeline-based, that is, have a date associated with the entry.

Figure 9:
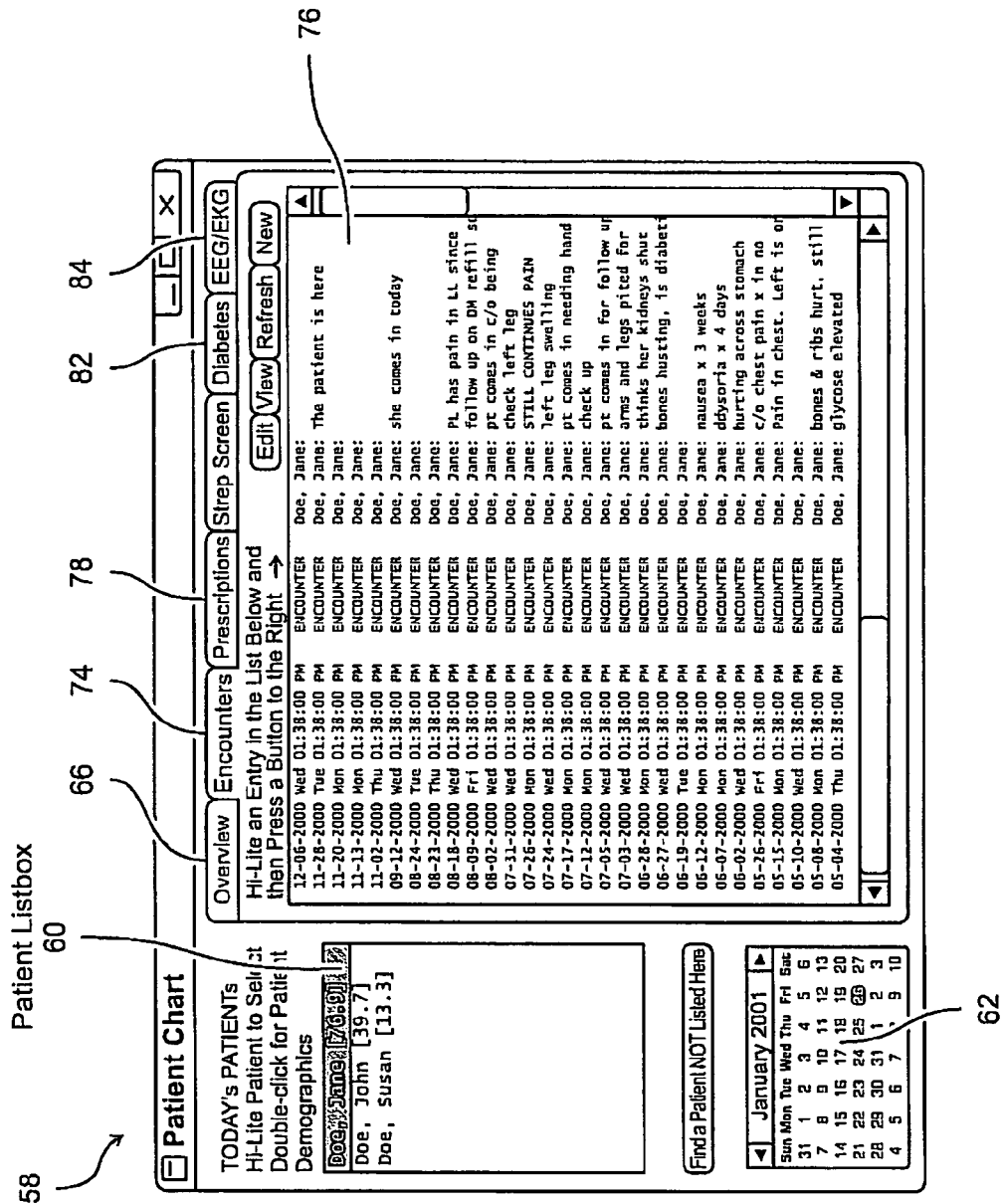
FIG. 9 illustrates the dialog box of FIG. 8 with an encounters tab selected.

As seen in FIG. 8, the overview list box includes boxes for displaying current problems 68, allergies 70, and medications 72, which information is drawn from the patient registration information entered upon addition of the patient to the system, as well as from updates subsequently entered during patient visits ("encounters"). FIG. 9 illustrates the Patient Chart dialog box 58 with an Encounters tab 74 selected. The dialog box 76 displayed with the Encounters tab 74 provides a listing of patient encounters which are listed in chronological order, starting from the most recent encounter. As can be seen in FIGS. 8 and 9, additional tabs are included for prescriptions 78, strep screen 80, diabetes 82 and EEG/EKG 84, which are default tabs for inclusion on the Patient Chart 58.

Figure 10:
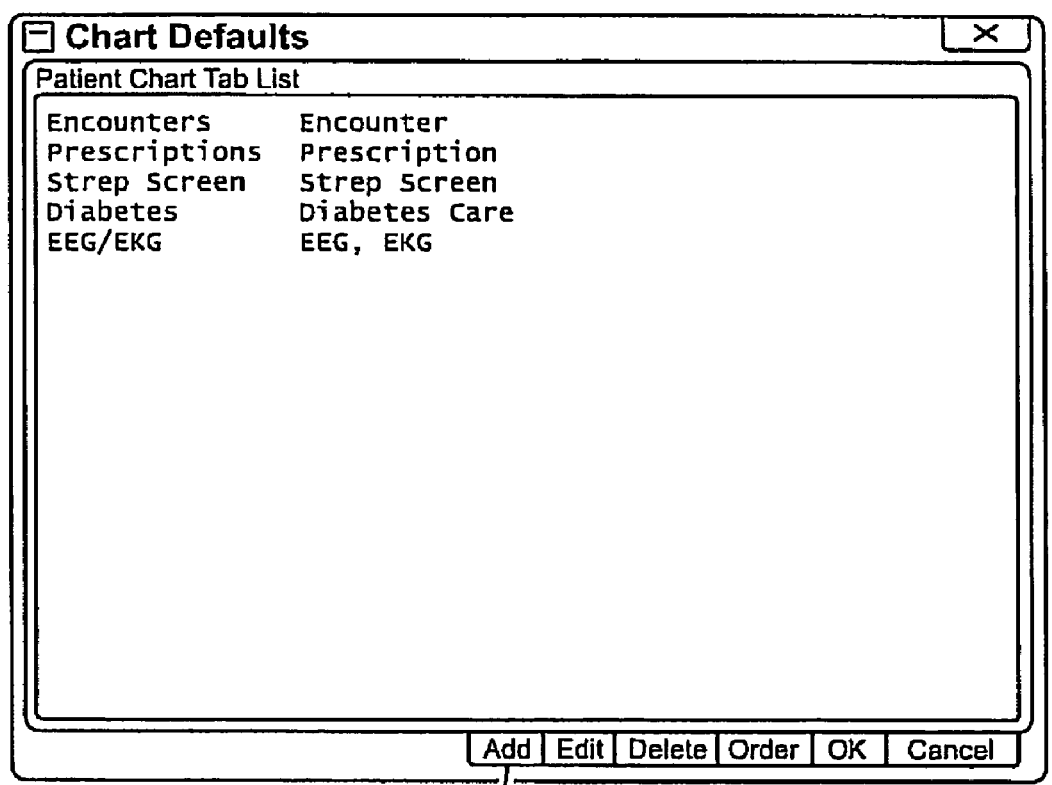
FIG. 10 illustrates a chart defaults box listing the default tabs for display on the patient chart of FIG. 8.
Figure 11:
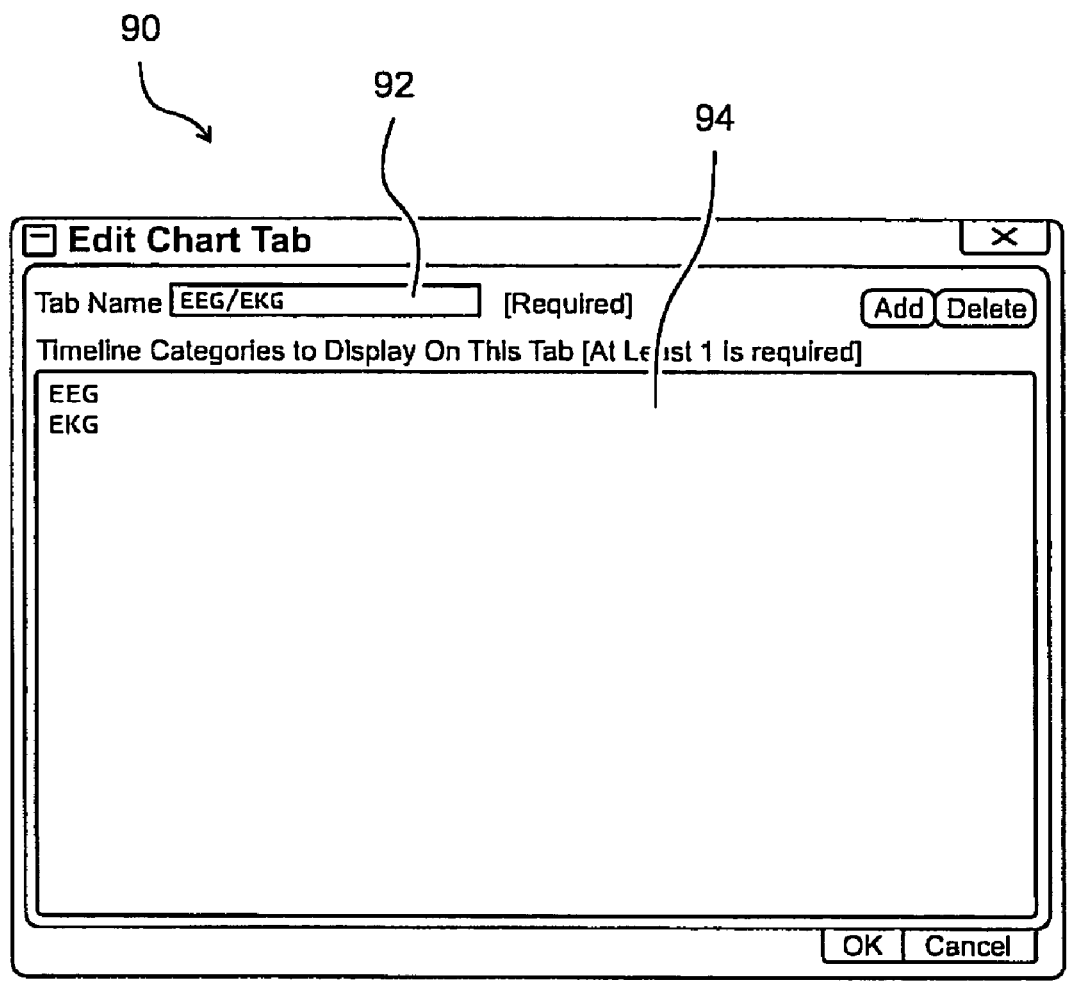
FIG. 11 illustrates a dialog box for adding a new chart tab to the patient chart of FIG. 8.
Figure 12:
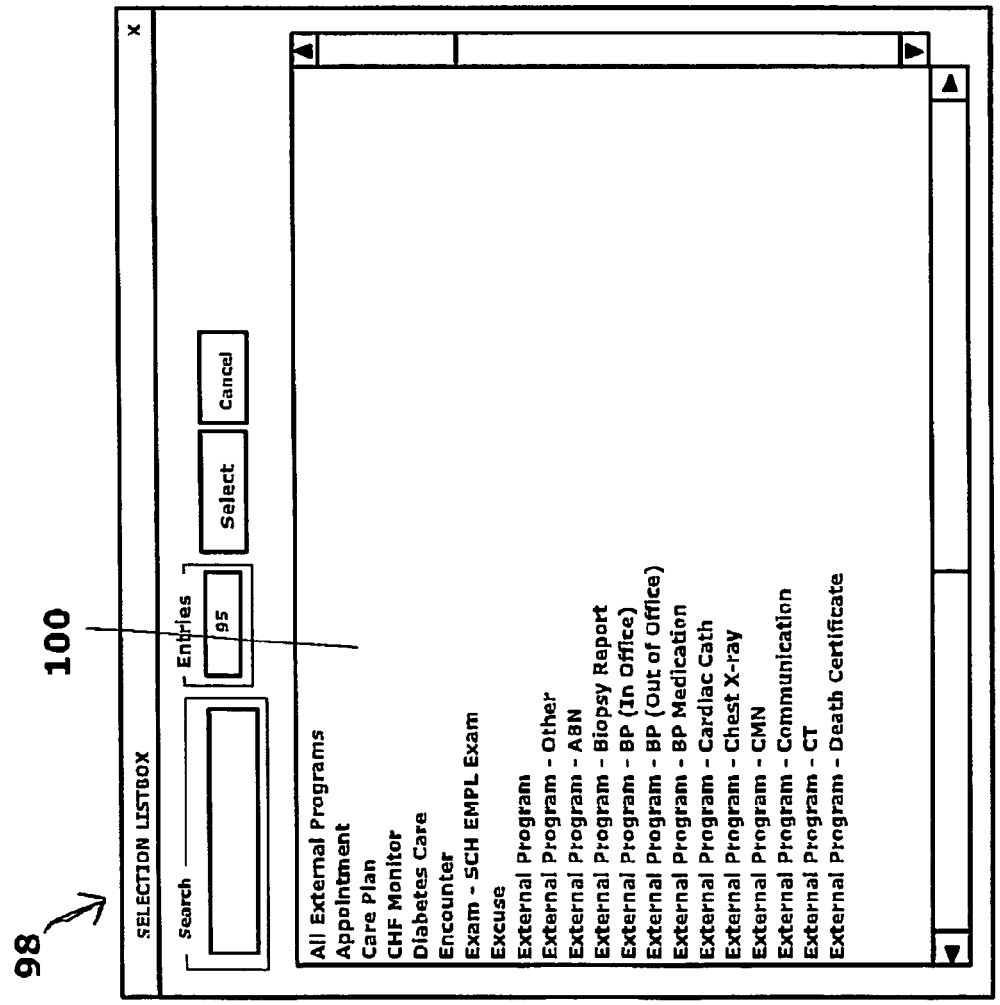
FIG. 12 illustrates a dialog box for selecting timeline categories to associate with the new tab selected through the dialog box of FIG. 11.

It should be understood that a characteristic of the present invention is provision of user capability to select tabs 64 to be displayed on the Patient Chart 58. This is accomplished by going through a series of dialog boxes illustrated in FIGS. 10-12. FIG. 10 shows a Chart Defaults box 86 which may be accessed from a utilities menu (not shown) of the system and preferably may be accessed only by the system administrator. The Chart Defaults box 86 normally includes a listing of the default tabs discussed above, and includes an Add button 88 for accessing the Edit 1 Chart Tab dialog box 90 illustrated in FIG. 11. In this dialog box 90, an edit field 92 is provided where a name for the new tab to be added is defined by the user, and the list box 94 for this dialog box 90 lists the timeline categories to be associated with the new tab. Selecting the Add button 96 from the Edit 1 Chart Tab dialog box 90 accesses a Selection dialog box 98, as shown in FIG. 12, which includes a list box 100 listing all possible timeline categories for the system, and any of the timeline categories may be selected for association with the new tab. It should also be noted that additional, user defined timeline categories may also be included in the Selection dialog box 98. Further, multiple tabs may be added to the Patient Chart 58 through the above-noted steps to provide ready access to the desired timeline categories or groups of categories. Accordingly, it should be apparent that the Patient Chart 58 for the system may be conveniently designed by the user to include selected timeline categories, and thereby accommodate the particular needs of the user.

Figure 13:
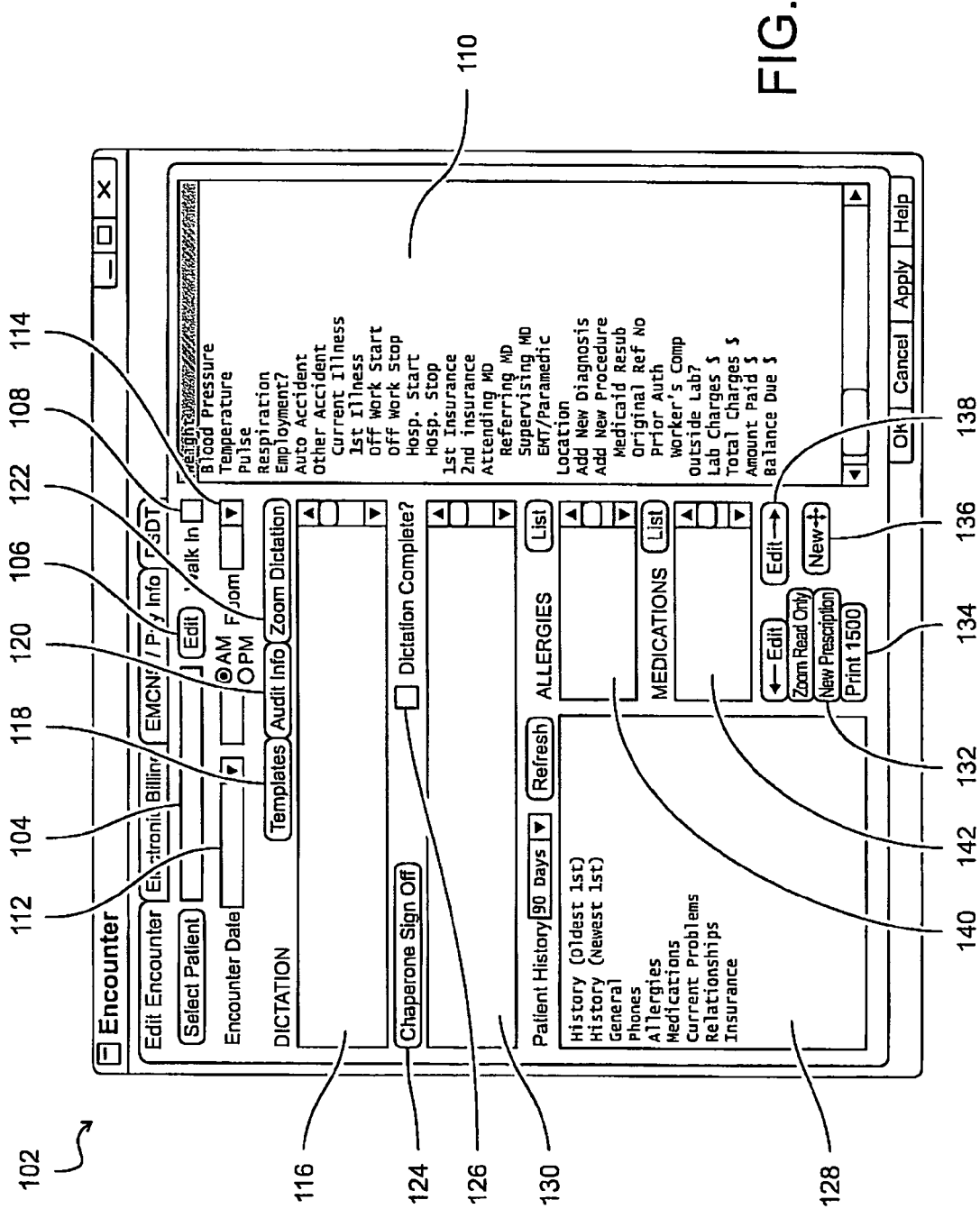
FIG. 13 illustrates an encounter dialog box used to define a patient encounter.

Referring to FIG. 13, an Encounter dialog box 102 is illustrated which is used to define a patient encounter. An encounter is a visit which is typically an examination of a patient by a physician, and encounters are billable events wherein electronic claims and HCFA-1500 forms are tied back to a specific encounter. The Encounter dialog box 102 provides a tool for gathering and accessing multiple categories of information about the patient. In particular, the encounter may include information on vital signs, physician dictation, insurance company information, charges, procedures, diagnoses, and HCFA-1500 form fields such as accident, worker's compensation, etc. The controls on the Encounter dialog box are defined as follows:

(a) Select Patient 104—For selecting a patient from the list of contacts in the system;

(b) Edit 106—If a Patient has been selected, pressing this button invokes the Contact Information dialog box 24 for the given patient;

(c) Walk-In 108—This box is checked if the Patient did not have an appointment;

(d) List 110—The list box on the right one-third of this dialog box contains a list of all Fields associated with the current encounter. Any field in this list box may be selected in order to change its contents. For example, selecting 'Add New Diagnosis' enables the user to add a new diagnosis to this encounter, selecting 'Add New Procedure' enables a user to add a new procedure to this encounter;

(e) Encounter Date (and time) 112—This box specifies the starting date and time of the encounter;

(f) Room 114—This box specifies the examination room number that this encounter will take place in. This is an optional field that may be used to help control patient flow through a medical facility;

(g) Dictation 116—This box is for entry of the physician's dictation and the dictation may be directly typed into this field. There are three buttons that aid in entering dictation:

(i) Templates 118—Selecting this button enables the user to access a Template dialog box (not shown). Templates are prewritten phrases organized in such a way to let the physician quickly enter dictation;

(ii) Audit Info 120—Selecting this button enables the user to access the system auditor which will examine the dictation for Medicare compliance. The physician can quickly see if his or her dictation supports the office/hospital visit procedure code selected for the current encounter;

(iii) Zoom Dictation 122—Selecting this button enables the user to display the dictation in a large dialog box for easy viewing;

(h) Chaperone Sign Off 124—This is an optional field whereby a chaperone who has accompanied the physician during the encounter can enter a password to sign off that the physician was never alone with the patient;

(i) Dictation Complete 126—This box is box is checked once the dictation is complete and ties back to the Timeline dialog box so that a physician can quickly see which encounters still require dictation;

(j) Patient History 128—This list box contains patient demographics, insurance, phone numbers, allergies, medications, current problems, family members, and all timeline entries for the selected patient. Any entry in this list may be selected in order to be displayed in a read-only field 130 immediately above the words 'Patient History'.

(k) New Prescription 132—This button is selected to male a new prescription for the selected patient;

(l) Print 1500 134—This button is selected to print an HCFA-1500 Form Insurance claim for this encounter;

(m) New 136—This button is selected to create a new Timeline entry for the selected patient;
(n) Edit 138—After selecting an entry in the list box on the right one-third of this dialog box, this button may be selected to edit that entry;
(o) Allergies 140—All of the selected patient's known allergies are listed here. Selecting the 'List' button enables the user to update and/or view the allergies;
(p) Medications 142—All of the Patient's known medications are listed here. Selecting the 'List' button enables the user to update and/or view the medications.

As noted above, diagnoses and procedures may be added to the encounter by selecting these fields in the list box 110. FIG. 14 illustrates a dialog box 144 listing commonly used diagnosis codes and from which diagnosis codes appropriate for the current encounter may be selected. FIG. 15 illustrates a dialog box 146 listing commonly used procedures and from which procedures appropriate for the current encounter may be selected. The selected diagnoses and procedures will then be displayed in the list box 110 of the Encounter dialog box 102.

Figure 16:
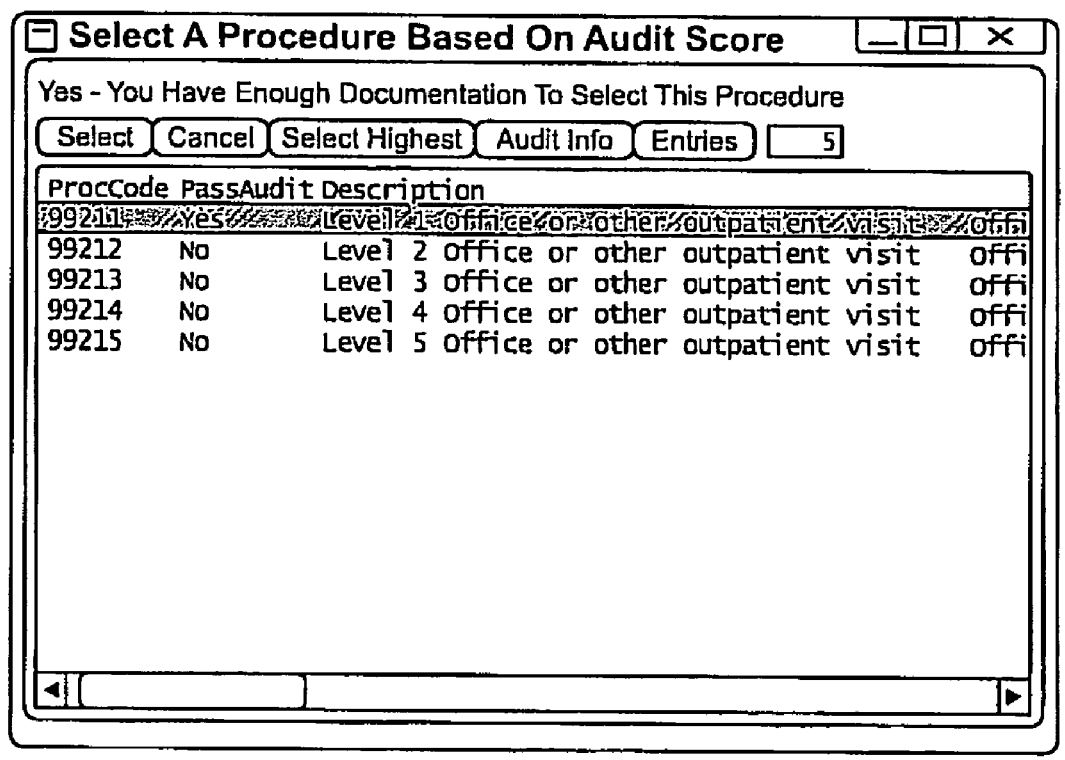
FIG. 16 illustrates a dialog box for providing a user with procedure code audit information.

If an 'office visit' or 'hospital visit' is selected for the procedure, and the code associated with the visit corresponds to one of a preselected group of procedure codes the system will display a further dialog box 148, such as is illustrated in FIG. 16, which box will automatically notify the user as to which office or hospital visits include enough documentation to support the selected procedures. This feature provides an automatic Medicare audit check in which 'Yes' label is associated with those procedures for which the entered documentation will likely pass the requirements of Medicare, and a 'No' label is applied to those that likely would not pass. This feature is useful to facilitate submitting claims for the highest available reimbursement level as well as to notify the user of possible need to include further documentation to support a higher level procedure.

Subsequently, after the procedure is selected, based on an audit, control passes to an Edit Procedure dialog box 150, as illustrated in FIG. 17. At this dialog box 150 defaults are filled in for the most commonly used fields, and the user is required to indicate supporting diagnoses for the selected procedure. In addition, the diagnosis codes 152 are identified and ordered by the user in the order of most important to least important such that the most important diagnoses will appear at the top of the list. Upon completion of this dialog box, the user is returned to the Encounter dialog box 102.

As noted above, the dictation entered by the physician may be input to the Encounter dialog box 102 through use of templates provided in a Template dialog box. The Template dialog box essentially provides pre-written phrases which may be selected as text for the physician to enter as dictation. The audit function of the system is designed to operate in conjunction with the pre-written phrases to enable the audit function to recognize the documentation entered through dictation and determine whether it meets Medicare requirements for the current procedure code selected for the encounter. Further, the physician may use the Audit Info button 120 to inquire whether the entered dictation is sufficient to support the selected procedure code. In this respect it should be noted that the Encounter dialog box 102 is preferably accessible by the physician concurrently with the patient encounter, whereby the patient is present in the event the physician finds that additional documentation relating to an examination or other information from the patient is required for support of the selected procedure code.

Figure 18:
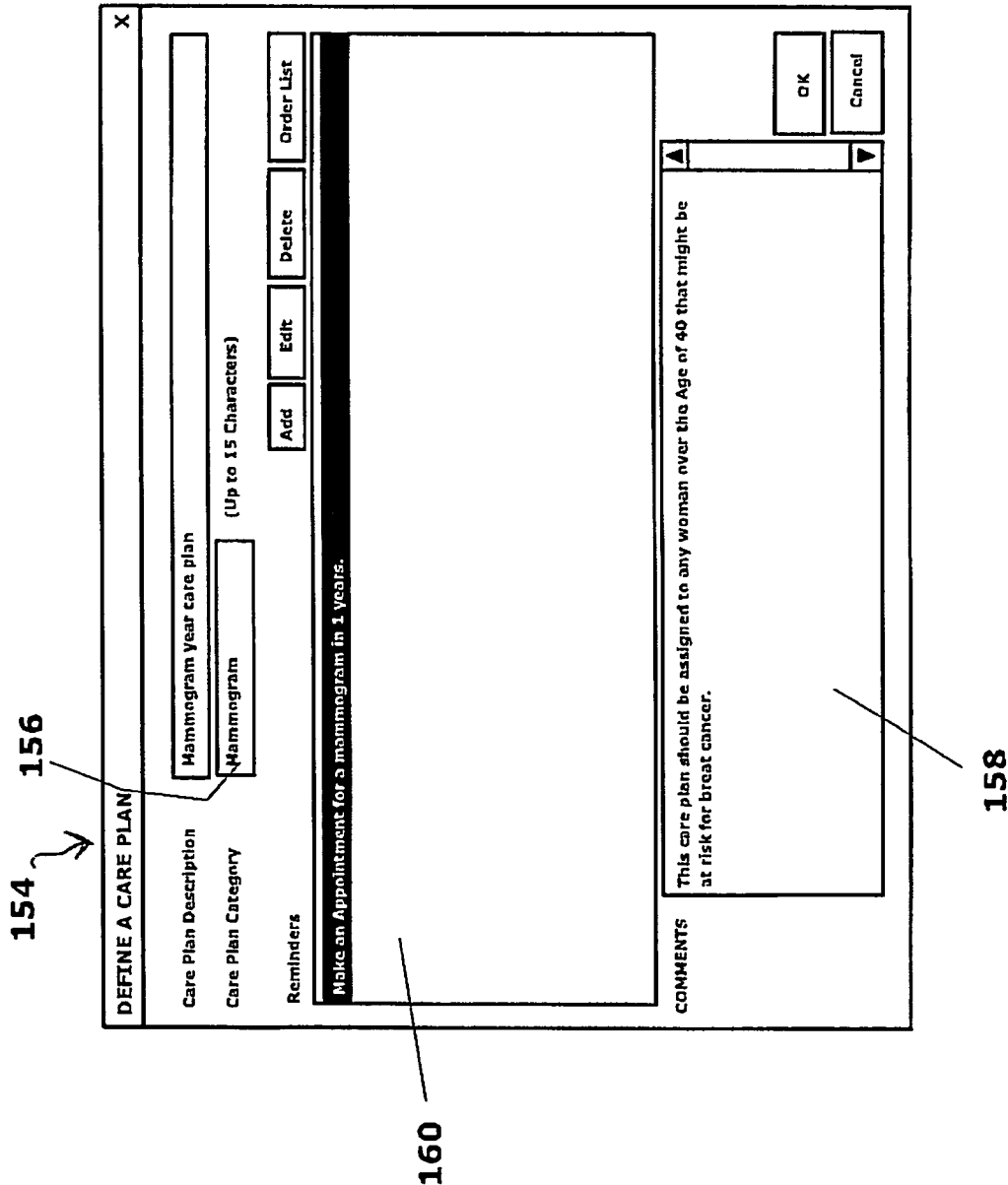
FIG. 18 illustrates a dialog box for enabling a user to define a care plan.

In another aspect of the present system, a care plan may be prepared for a patient, or assigned to a patient from a list of saved care plans. A care plan is a future plan of action on behalf of a specific patient and is formed by a group of reminders wherein a reminder is created to remind the user of a timeline event which will occur at a particular date and time in the future. More specifically, a care plan provides the user, such as a physician, with a proactive tool for tracking a patient's condition over time and provides call-ups or reminders at time intervals and frequencies predetermined by the user. For example, referring to FIG. 18, an initial Care Plan dialog box 154 is shown which enables the user to define a care plan, such as a five year care plan for women who need to have a mammogram on a yearly basis, and includes an edit field 156 for defining a care plan category, entering a care plan description (comments 158) and entering reminder events 160. FIG. 19 illustrates a dialog box 162 for entering details of the reminder such as length of time to the initial reminder (1 year), number of times the reminder should be repeated (4 additional reminders), and time interval between reminders (1 year). FIG. 20 illustrates the dialog box 162 with a further reminder which would be included in the current example and reminds the user that the care plan is expiring after five years, and consider implementing an appropriate further care plan. It should be understood that a variety of care plans may be created to cover different conditions, such as obesity, high cholesterol, hypertension, etc.

Care plans are incorporated into a particular patient's timeline by referencing the list of saved care plans, in particular referencing a care plan dictionary, and selecting appropriate care plans for the particular patient. The care plan time entries will then appear when the Timeline tab 38 is selected in the Contact Information dialog box 24 (FIG. 6).

As noted previously dictionaries include information which does not change substantially over time, and typically includes information which may be referenced for entry a plurality of times during use of the system. In the case of care plans, different patients having similar conditions are often placed on similar schedules for treatment and follow-up, and the provision of a care plan dictionary reduces time required for data entry and facilitates scheduling of future encounters related to the condition. Other dictionaries included with the system and their descriptions comprise the following:

Procedure Codes Dictionary—stores all procedure codes, descriptions, and pricing information. Procedures are assigned to encounters to document a billable service performed by a medical office on behalf of a patient.

Diagnosis Codes Dictionary—stores all diagnosis codes, and descriptions.

Diagnoses are assigned to encounters to document a medical diagnosis of a patient's current health.

Classification Dictionary—stores classifications that may be assigned to a classifications include patient, physician, nurse, insurance company, cardiology MD, health care provider, lab, etc.

Prescription Dictionary—stores a collection of standard prescriptions that the user can quickly copy from. Use of the prescription dictionary enables the user to only have to type in the medication, dosage, and directions for a prescription one time.

Requisition Dictionary—stores a list of all of the commonly used requisition types in your office, where a requisition is an in-house request to perform some type of service on behalf of a patient and comprises an entry in a patient's timeline.

Billing Codes Dictionaries—stores billing code information and is broken down into five different billing codes dictionaries:

1. Insurance Class Dictionary.
2. Payment Codes Dictionary.
3. Medicare claim Adjustment Codes.
4. Medicare Reference Codes.
5. Medicare Inpatient/Outpatient Codes.

Status Dictionaries—used to maintain the past and current statuses of three different classes of events. There are three different status dictionaries:
  1. Appointment Status—used to maintain the current and past statuses of appointments (e.g. scheduled, late, canceled).
  2. Encounter Status—used to maintain the current and past statuses of encounters (e.g. scheduled, nurse, doctor, check-out). Useful for tracking patients after entry to a medical facility wherein each patient encounter in the facility would be assigned one of the following statuses: Scheduled, Exam Room, Doctor, Check Out, and Discharged.
  3. User Defined Status—used to maintain the current and past statuses of user defined timeline records, such as lab tests (e.g. scheduled, in-process, complete).

HCFA-1500 Codes Dictionaries—stores code information for inclusion ill the HCFA-1500 form including: 1) Place Of Service Codes, and 2) Type Of Service Codes.

Referral Dictionary—stores instructions used when referring a patient to another office or physician. Such instructions may need to include steps for a patient to follow in preparation for procedure, such as a gall bladder ultrasound, or upper GI, and these instructions are included in the referral dictionary.

Relationship Dictionary—stores a defined relationship or association between two contact, and typically stores family ties, such as parent, brother, aunt, etc.

Exam Room Numbers Dictionary—stores a list of exam room numbers or identifiers for exam rooms in a medical facility, and in particular in a smaller practice.

Phone Descriptions Dictionary—stores the different types of phone descriptions that may need to be documented for a contact. Phone descriptions include home, office, fax, cell, emergency, etc.

Appointment Reasons Dictionary—stores a list of the most common reasons patients make an appointment with a medical facility.

Physicians Dictionary—stores information on physicians or other health care providers that may be assigned identification numbers by insurance companies and/or governing medical boards. The physicians dictionary is used to keep track of insurance identification numbers (e.g. PIN, GRP), assignment status, and similar information.

Equipment Dictionary—stores information for tracking equipment and machinery in a medical facility. Enables assignment and tracking of equipment to patients, physicians, nurses, rooms, departments, floors, etc.

Location Dictionary—stores a list of locations in a facility and including information such as status of use. This dictionary and is particularly intended for use in tracking rooms or locations in larger facilities such as hospitals which may have several buildings, wings and floors.

Assignment Dictionary—stores information relating to a temporary association between two entities and this dictionary is typically used in a hospital setting. Examples of assignments include assignment of a patient to a bed, assignment of a nurse to a patient, assignment of a nurse to a floor/wing/unit/department, and assignment of equipment to a room.

Fee Schedules Dictionary—stores fee schedule for use in setting different prices for the same procedure or miscellaneous charge. For example, the user may choose to charge Medicaid patients one price for an office visit, commercially insured patients another price, and private-pay patients yet a third price.

Miscellaneous Charges Dictionary—stores a list of items that should be charged directly to a contact, and such as items which are not necessarily medically related, i.e., a bill for making several copies of a patient's medical records.

Accordingly, it can be seen that the dictionaries for the present system enable the user to configure the system to the user's particular needs, such as by including certain desired items through edits to the dictionaries, or by selecting certain items from the dictionary to be implemented, such as in a patient timeline. Further, additional dictionaries may be created by the user to meet the user's particular needs, and the present system is particularly conducive to development of the dictionaries as the system is used, such as through the development of care plans administered to the patients of the user.

While the method and system herein described constitute a preferred embodiment of this invention, it is to be understood that the invention is not limited to this precise method and system and that changes may be made without departing from the scope of the invention, which is defined in the appended claims.

What is claimed is:

1. A method of managing a patient encounter using an electronic medical records system for use by medical personnel within a medical facility, the method comprising:
  a plurality of medical personnel collecting and storing individual patient medical information in specified fields on a computer;
  assigning an office visit procedure code level to an encounter with a patient;
  entering documentation of the encounter with the patient;
  performing an audit of the documentation during the encounter with the patient; and
  providing an indication to a user of a requirement to provide additional documentation to support the assigned procedure code level.

2. The method of claim 1 including editing the documentation during the patient encounter in response to the indication of a need to provide additional documentation.

3. The method of claim 2 wherein the step of editing the documentation includes interacting with the patient to obtain additional information.

4. The method of claim 1 including the step of providing an indication of additional information required to support the assigned procedure code level.

5. The method of claim 1 wherein the step of entering documentation comprises entering dictation from a physician.

6. The method of claim 5 wherein the dictation is entered from text phrases contained in templates and selected by the user for entry in to the documentation of the encounter.

7. The method of claim 6 wherein the templates include text phrases provided by the physician at a time prior to the encounter.

8. The method of claim 1 wherein the audit comprises determining compliance of the documentation with Medicare requirements.

9. A method of managing a patient encounter using an electronic medical records system, the method comprising:

providing a care plan dialog screen for creating a time based care plan;

a medical services provider entering a care plan description at the care plan dialog screen;

entering a care plan category at the care plan dialog screen;

entering at least one reminder event for inclusion in the care plan by providing a path from the care plan dialog screen to a care plan reminder definition screen; and entering a lead time, defining a time interval providing an initial reminder to a patient, from the reminder definition screen.

10. The method of claim 9 including entering a repeat count number, defining a number of additional reminders to be created, from the reminder definition screen.

11. The method of claim 10 including entering a repeat interval time, defining a time interval for providing the additional reminders to a patient, from the reminder definition screen.

12. The method of claim 1 including saving a plurality of care plans in a care plan dictionary and assigning at least one care plan to a patient.

13. The method of claim 12 wherein the at least one care plan is assigned to a plurality of patients.

* * * * *